United States Patent

Roby et al.

[11] Patent Number: 6,007,565
[45] Date of Patent: Dec. 28, 1999

[54] ABSORBABLE BLOCK COPOLYMERS AND SURGICAL ARTICLES FABRICATED THEREFROM

[75] Inventors: Mark Roby, Killingworth; Ying Jiang, North Haven, both of Conn.

[73] Assignee: United States Surgical, Norwalk, Conn.

[21] Appl. No.: 08/924,359

[22] Filed: Sep. 5, 1997

[51] Int. Cl.$^6$ .................................................. A61B 17/00
[52] U.S. Cl. ............................................................ 606/228
[58] Field of Search ................................... 606/228–231; 525/415; 528/354

[56] References Cited

U.S. PATENT DOCUMENTS

| | | |
|---|---|---|
| 2,668,162 | 2/1954 | Lowe . |
| 2,683,136 | 7/1954 | Higgins . |
| 2,703,316 | 3/1955 | Schneider . |
| 2,758,987 | 8/1956 | Salzberg . |
| 3,225,766 | 12/1965 | Baptist et al. . |
| 3,268,486 | 8/1966 | Klootwijk . |
| 3,268,487 | 8/1966 | Klootwijk . |
| 3,297,033 | 1/1967 | Schmitt . |
| 3,422,181 | 1/1969 | Chirgwin, Jr. . |
| 3,442,871 | 5/1969 | Schmitt et al. . |
| 3,463,158 | 8/1969 | Schmitt et al. . |
| 3,468,853 | 9/1969 | Schmitt et al. . |
| 3,531,519 | 9/1970 | Parkin et al. . |
| 3,565,869 | 2/1971 | DeProspero . |
| 3,597,449 | 8/1971 | DeProspero et al. . |
| 3,620,218 | 11/1971 | Schmitt et al. . |
| 3,626,948 | 12/1971 | Glick et al. . |
| 3,636,956 | 1/1972 | Schneider . |
| 3,733,919 | 5/1973 | Rupp, II . |
| 3,736,646 | 6/1973 | Schmitt et al. . |
| 3,772,420 | 11/1973 | Glick et al. . |
| 3,781,349 | 12/1973 | Ramsey et al. . |
| 3,784,585 | 1/1974 | Schmitt, et al. . |
| 3,792,010 | 2/1974 | Wasserman et al. . |
| 3,797,499 | 3/1974 | Schneider . |
| 3,839,297 | 10/1974 | Wasserman et al. . |
| 3,846,382 | 11/1974 | Ramsey et al. . |
| 3,867,190 | 2/1975 | Schmitt et al. . |
| 3,878,284 | 4/1975 | Schmitt et al. . |
| 3,902,497 | 9/1975 | Casey . |
| 3,937,223 | 2/1976 | Roth . |
| 3,982,543 | 9/1976 | Schmitt et al. . |
| 3,987,937 | 10/1976 | Coucher . |
| 4,033,938 | 7/1977 | Augurt et al. . |
| 4,045,418 | 8/1977 | Sinclair . |
| 4,052,988 | 10/1977 | Doddi et al. . |
| 4,057,537 | 11/1977 | Sinclair . |
| 4,060,089 | 11/1977 | Noiles . |
| 4,137,921 | 2/1979 | Okuzumi et al. . |
| 4,157,437 | 6/1979 | Okuzumi et al. . |
| 4,243,775 | 1/1981 | Rosensaft et al. . |
| 4,246,904 | 1/1981 | Kaplan . |

(List continued on next page.)

FOREIGN PATENT DOCUMENTS

| | | |
|---|---|---|
| 779291 | 7/1957 | United Kingdom . |
| 1332505 | 10/1973 | United Kingdom . |
| 1414600 | 11/1975 | United Kingdom . |
| 2102827 | 2/1983 | United Kingdom . |

OTHER PUBLICATIONS

Biodegradable polymers for use in surgery—polyglycolic/poly(actic acid) home—and copolymers:1; Polymer; D.K. Gilding and A.M. Reed; Dec. 1979; vol. 20; pp. 1459–1464.

*Primary Examiner*—Michael Buiz
*Assistant Examiner*—Vikki Trinh

[57] ABSTRACT

Block copolymers wherein the first block contains from about 40 to about 65 mole percent of repeating units derived from glycolide randomly combined with from about 60 to 35 mole percent of repeating units derived from lactide and the second block contains repeating units derived from glycolide and repeating units derived from lactide, the second block containing a higher proportion of repeating units derived from glycolide than the first block, with units derived from glycolide constituting from about 75 to about 95 mole percent of the entire block copolymer are useful in forming surgical articles, including sutures.

10 Claims, 1 Drawing Sheet

U.S. PATENT DOCUMENTS

| | | |
|---|---|---|
| 4,273,920 | 6/1981 | Nevin . |
| 4,275,813 | 6/1981 | Noiles . |
| 4,279,249 | 7/1981 | Vert et al. . |
| 4,300,565 | 11/1981 | Rosensaft et al. . |
| 4,429,080 | 1/1984 | Casey et al. . |
| 4,526,938 | 7/1985 | Churchill et al. . |
| 5,019,093 | 5/1991 | Kaplan et al. .......................... 606/228 |
| 5,059,213 | 10/1991 | Chesterfield et al. .................. 606/228 |
| 5,133,739 | 7/1992 | Bezwada et al. . |
| 5,252,701 | 10/1993 | Jarrett et al. . |
| 5,403,347 | 4/1995 | Roby et al. . |
| 5,431,679 | 7/1995 | Bennett et al. . |
| 5,502,159 | 3/1996 | Liu et al. . |
| 5,522,841 | 6/1996 | Roby et al. . |
| 5,554,170 | 9/1996 | Roby et al. . |

FIG_1
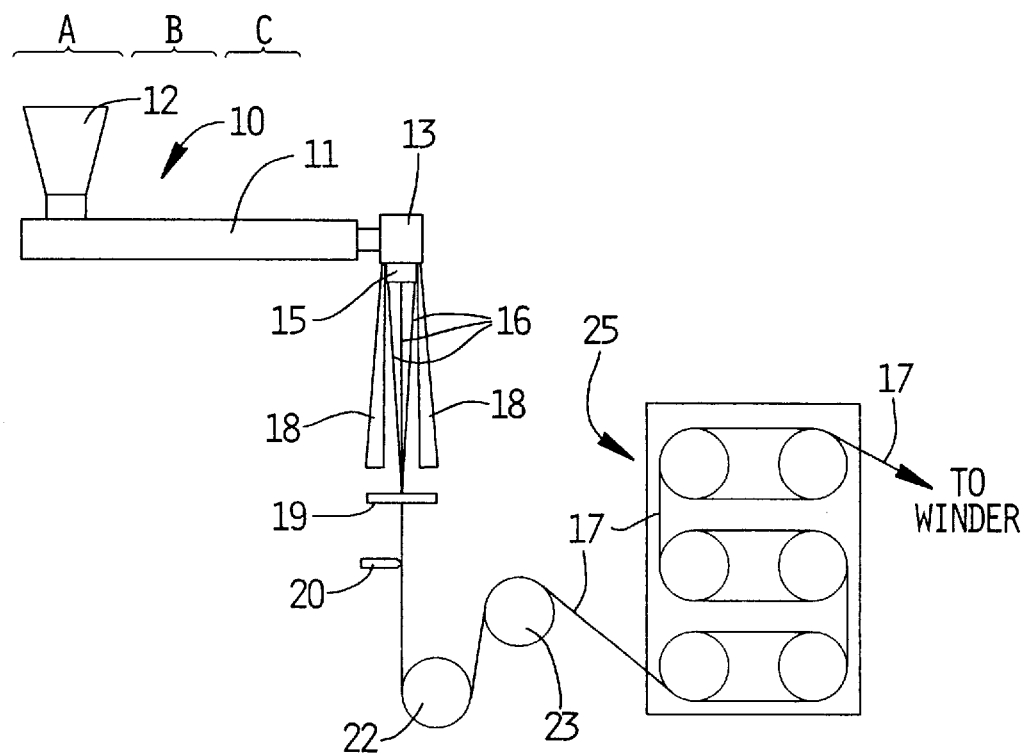
FIG_2
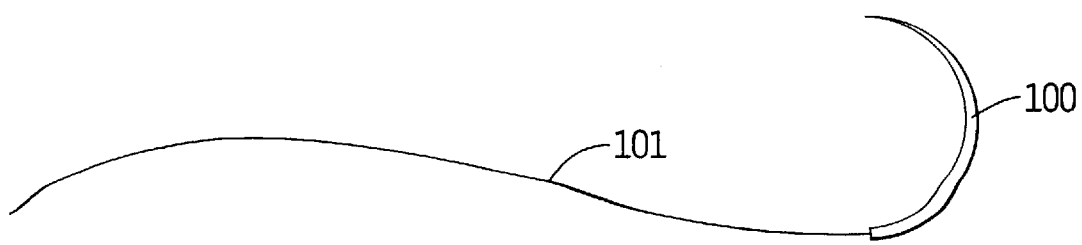

ABSORBABLE BLOCK COPOLYMERS AND SURGICAL ARTICLES FABRICATED THEREFROM

TECHNICAL FIELD

Absorbable block copolymers having one of the blocks made from randomly polymerized glycolide and lactide and another block made substantially entirely from glycolide are described. Processes for making the copolymers and surgical articles made totally or in part from such copolymers, including sutures, are also described.

BACKGROUND

Bioabsorbable surgical devices such as, for example, sutures, made from copolymers derived from glycolide and lactide are known in the art.

A desirable characteristic of a bioabsorbable suture is its ability to exhibit and maintain desired tensile properties for a predetermined time period followed by rapid absorption of the suture mass (hereinafter "mass loss".)

Absorbable multifilament sutures such as DEXON sutures (made from glycolide homopolymer and commercially available from Davis & Geck, Danbury, Conn.), VICRYL sutures (made from a copolymer of glycolide and lactide and commercially available from Ethicon, Inc., Sommerville, N.J.), and POLYSORB sutures (also made from a copolymer of glycolide and lactide and commercially available from United States Surgical Corporation, Norwalk, Conn.) are known in the industry as short term absorbable sutures. The classification short term absorbable sutures generally refers to surgical sutures which retain at least about 20 percent of their original strength at three weeks after implantation, with the suture mass being essentially absorbed in the body within about 60 to 90 days post implantation.

Early attempts to increase in vivo strength retention have resulted in monofilament sutures, which are generally classified as long term absorbable sutures capable of retaining at least about 20 percent of their original strength for six or more weeks after implantation, with the suture mass being essentially absorbed in the body within about 180 days post implantation. For example, PDS II sutures (commercially available from Ethicon, Inc., Sommerville, N.J.), are synthetic absorbable monofilament sutures that reportedly retain at least about 20 to 30 percent of its original strength six weeks after implantation. However, PDS II reportedly exhibits minimal mass loss until 90 days after implantation with the suture mass being essentially absorbed in the body about 180 days after implantation. MAXON suture (commercially available from Davis & Geck, Danbury, Conn.) is another absorbable synthetic monofilament that reportedly generally fits this absorption profile.

Later attempts to provide an acceptable absorbable monofilament sutures resulted in MONOCRYL sutures, a suture available from Ethicon, Inc.

Most recently, United States Surgical Corporation has introduced BIOSYN monofilament sutures which exhibit good flexibility, handling characteristics, knot strength and absorption characteristics similar to those of presently available short term absorbable multifilament sutures.

It would be advantageous to provide a bioabsorbable synthetic multifilament surgical suture which exhibits and maintains tensile properties and handling characteristics comparable to commercially available short term absorbable multifilament sutures, while having increased in vivo strength retention without substantially increasing the time at which the suture mass is absorbed in the body.

SUMMARY

It has now surprisingly been found that absorbable surgical articles formed from a block copolymer having one of the blocks made from a random copolymer of glycolide and lactide and another block made from a predominant amount of glycolide combined with lactide exhibit increased in vivo strength retention without exhibiting any substantial decrease in the rate of bioabsorption as measured by mass loss. Preferably, the block copolymers used in forming surgical articles include one block having between about 40 and about 65 mole percent of glycolic acid ester units and between about 60 and 35 mole percent of lactic acid ester units, and glycolic acid ester units constitute from about 75 to about 95 mole percent of the overall block copolymers.

The copolymers are prepared by first copolymerizing glycolide and lactide to form a random prepolymer. Glycolide is then added to the reaction vessel and combines with the random prepolymer and any residual unreacted monomer to produce a block copolymer.

In particularly useful embodiments, the block copolymers can be spun into fibers. The fibers can be advantageously fabricated into braided multifilament sutures.

BRIEF DESCRIPTION OF THE DRAWINGS

FIG. 1 is a schematic illustration of an apparatus which is suitable for manufacturing multifilament yarns in accordance with this disclosure.

FIG. 2 is a perspective view of a suture made using the copolymers described herein attached to a needle.

DESCRIPTION OF THE PREFERRED EMBODIMENTS

It has been found that a block copolymer having two specific types of blocks, an "A" block having a proportion of glycolic acid ester linkages randomly combined with lactic acid ester linkages and a "B" block including glycolic acid ester linkages can advantageously be combined to form a block copolymer useful in forming surgical elements.

The block copolymers include an A block formed from a copolymer which has repeating units derived from glycolide randomly combined with repeating units derived from lactide. Repeating units derived from glycolide comprise between about 5 and about 95 mole percent of the first block and preferably about 40 to about 65 mole percent of the first block. Most preferably, glycolide comprises about 55 to about 60 mole percent of the first block. Copolymers of glycolide and lactide having an inherent viscosity of from about 0.6 to about 1.7 dl/g measured at 30° C. and at a concentration of 0.25 g/dl in chloroform or HFIP may generally be used as the first block.

The B block of the copolymer comprises glycolide. Preferably glycolide comprises at least about 80 mole percent, and more preferably greater than about 85 mole percent of the B block. Most preferably, the B block comprises greater than about 90 mole percent glycolide.

The block copolymers can be made using any technique known to those skilled in the art. Thus, for example, each block can be individually formed as a prepolymer and then the prepolymers can be reacted to form the desired block copolymer. In a particularly useful embodiment, the copolymer is prepared by first preparing a statistical pre-polymer made from glycolide and lactide. The prepolymer can be prepared using conventional techniques. For example, monomers can be dried, mixed in a reaction vessel with an initiator (either a single or multi-functional initiator) and a suitable polymerization catalyst and heated at temperatures from about 160° C. to about 180° C. for a period of time ranging from about 4 hours to about 6 hours. Then, glycolide is added directly to the reactor and reacts with the prepolymer and any residual monomer to thereby form the block copolymer. Preferably, glycolide is added and polymerized at temperatures from about 190° C. to about 220° C. for a time varying between about 1 and 3 hours from the time addition of the glycolide is complete. It should be understood that a combination of glycolide and lactide can be added to form the second block provided the overall composition of the block copolymer is as described herein.

In forming the block copolymers, the A block may be present in an amount from about 10 to about 60 percent by weight based on the weight of the final block copolymer. The B block may be present in an amount from about 40 to about 90 weight percent based on the weight of the final block copolymer. Preferably, the A block comprises between about 25 and about 40 weight percent of the block copolymer. In a particularly useful embodiment, the A block comprises about 30 weight percent and the B block comprises about 70 weight percent of the final block copolymer. The copolymers can have a molecular weight such that their inherent viscosity is from about 1.1 to about 2 dl/g, and preferably from about 1.3 to about 1.6 dl/g measured at 30° C. at a concentration of 0.25 g/dl in hexafluoroisopropanol (HFIP).

The block copolymers may have repeating block units such as AB, BAB, and any combination thereof, such as e.g., BABAB, with AB being preferred.

The block copolymers can be formed into surgical articles using any known technique, such as, for example, extrusion, molding and/or solvent casting. The copolymers can be used alone, blended with other absorbable compositions, or in combination with non-absorbable components. A wide variety of surgical articles can be manufactured from the copolymers described herein. These include but are not limited to clips and other fasteners, staples, sutures, pins, screws, prosthetic devices, wound dressings, drug delivery devices, anastomosis rings, and other implantable devices. Fibers made from the present copolymers can be knitted, woven or made into non-woven materials with other fibers, either absorbable or nonabsorbable to form fabrics, such as meshes and felts. Compositions including these block copolymers can also be used as an absorbable coating for surgical devices. Preferably, however, the copolymers are spun into fibers to be used in making sutures.

FIG. 1 schematically illustrates a filament manufacturing operation suitable for use with the polymers described herein. Extruder unit 10 is of a known or conventional type and is equipped with controls for regulating the temperature of barrel 11 in various zones thereof, e.g., progressively higher temperatures in three consecutive zones A, B and C. along the length of the barrel. Pellets or powder of resin to be spun into filaments are introduced to the extruder through hopper 12. Any of the polymeric resins which are useful for the formation of fibers can be used herein.

Motor-driven metering pump 13 delivers extruded resin at a constant rate through spinneret 15 possessing one or more orifices of desired diameter to provide a plurality of molten filaments 16. While spinneret 15 is shown schematically in FIG. 1 as extruding three filaments, it should be understood that the spinneret may extrude anywhere from 1 to 200 or more filaments simultaneously.

The filaments 16 travel downward and are gathered together by guide 19 to produce a yarn 17. The distance the filaments 16 travel after emerging from spinneret 15 to the point where they contact guide 19, i.e., the air gap, can vary and can advantageously be from about 0.5 m to about 10 m and preferably from about 1 m to about 2 m. A chimney 18, or shield, can be provided to isolate filaments 16 from contact by air currents which might otherwise affect the cooling or movement of the filaments in some unpredictable manner. In general, the temperature of zones A, B and C of the barrel 11 will vary depending on a number of factors such as the size of the powder or pellets and the rate of feed.

Once filaments 16 are gathered together by guide 19 to produce yarn 17, a spin finish can be applied to yarn 17, if desired, using any known technique.

As shown in FIG. 1, the yarn may be wrapped around a lub godet 22 and one or more additional godets, for example, godet 23, to take up and adjust the tension on the yarn. The yarn 17 may then be passed to a heated draw frame 25. Draw frame 25 may be of any configuration. As shown in FIG. 1, draw frame 25 can include three pairs of godets which can be used to stretch the yarn or to allow relaxation and perhaps shrinkage of yarn 17. The speed at which the godets rotate and the temperature at which the draw frame is maintained will determine the amount of stretching and/or relaxation which occurs. Setting the various speeds and temperatures to achieve a desired result is within the purview of those skilled in the art.

Table I provides suitable ranges of values for spinning and stretching parameters useful in producing yarns from the present copolymers.

TABLE I

MELT SPINNING APPARATUS AND
OPERATING CONDITIONS

| Apparatus Component, Operating Parameter | |
|---|---|
| Extruder barrel temp., zone A, ° C. | 200–250 |
| Extruder barrel temp., zone B, ° C. | 200–250 |
| Extruder barrel temp., zone C, ° C. | 200–250 |
| Extruder barrel pressure, psi | 700–2500 |
| Extruder barrel melt temp., ° C. | 200–260 |
| Pump size, cc per rev. | .16–.584 |
| Pump rpm | 10–50 for size .16 pump |
| | 3–11 size .584 pump |
| Pump temp., ° C. | 200–250 |
| Pump pressure, psi | 500–2500 |
| Pump melt temp.,° C. | 200–250 |
| Block temp., ° C. | 200–250 |
| Clamp temp., ° C. | 200–250 |
| Adapter temp., ° C. | 200–250 |
| Candle filter, screen, microns | 10–60 |
| No. of spinneret | 5–200 |
| Diameter of spinneret orifices, .001 in | 5–30 |
| Spinneret temp., ° C. | 200–250 |
| Spinneret pressure, psi | 500–2500 |
| Spinneret melt temp., ° C. | 200–250 |
| cc/hr output, per spinneret | 5–20 |
| First pair of godets, ° C. | 50–90 |
| First pair of godets, mpm | 80–275 |
| Second pair of godets, ° C. | 60–140 |
| Second pair of godets, mpm | 675–1610 |
| Draw (stretch) ratio | 2–6 |
| Third pair of godets, ° C. | ambient |
| Third pair of godets, mpm | 750–1400 |
| Shrinkage (relaxation), percent | 5–10 |

After drawing, the yarn may be sent to a winder where it can be placed onto spools for storage while awaiting further treatment and/or braiding. Any spin finish can be removed from the yarn by washing.

Sutures made from the copolymers described herein can be prepared by methods known in the art. Braid constructions and methods suitable for making multifilament suture using the copolymers described herein include those disclosed in U.S. Pat. Nos. 5,059,213 and 5,019,093. The characteristics of the braided suture prepared in accordance with this disclosure, apart from the material of its construction, may include:

(1) overall suture denier;
(2) the pattern of the interlocking yarns expressed as the pick count, which is to say, the number of crossovers of individual sheath yarns per linear inch of suture;
(3) the number of sheath yarns comprising the braid;
(4) the denier of the individual filaments comprising each sheath yarn; and,
(5) the denier of the core, where present.

(1) Overall Denier of the Suture

The overall denier of the braided suture can vary from about 25 to about 4300. Within this range, the ranges of overall denier for particular sutures are: from about 25 to about 80 denier; from above about 80 to about 150 denier; from above about 150 to about 300 denier; from above about 300 to about 600 denier; from above about 600 to about 950 denier; from above about 950 to about 1500 denier; from above about 1500 to about 2300 denier; and, from above about 2300 to about 4300 denier.

(2) Pattern of the Interlocking Sheath Yarns (Pick Count)

For a suture of any range of overall denier, pick count can vary from about 25 to about 100 crossovers/inch with about 40–85 crossovers/inch being preferred. For sutures constructed within any range of overall denier, as larger numbers of sheath yarns are employed, the pick-count for acceptable sutures will also increase within the above ranges.

For a suture of a particular range of denier and number of sheath yarns, pick count is advantageously established to achieve a balance in the properties desired. In general, with increasing pick count, surface roughness of the suture tends to increase and with decreasing pick count, the ability of the external braided sheath to contain the core (if present) tends to decrease even reaching the point where the braid may become so loose as to result in the core protruding therethrough.

(3) The Number of Sheath Yarns

The number of sheath yarns bears some relation to overall suture denier, the number generally increasing with the weight of the suture. Thus, across the range of suture weight (denier) indicated above, the braided suture of this invention can be constructed with from about 3 up to as many as about 36 individual sheath yarns constructed from individual filaments having the deniers discussed below.

Table II below sets forth broad and preferred ranges for the numbers of sheath yarns which are suitable for the construction of braided sutures of various ranges of overall denier. The pick counts of the sutures vary from about 50 to about 100 crossovers/inch and deniers of individual filaments vary from about 0.2 to about 6.0 for the broad range of number of sheath yarns and the pick counts vary from about 55 to about 80 and the deniers of individual filaments vary from about 0.8 to about 3.0, and advantageously from about 0.8 to about 1.6, for the preferred range of number of sheath yarns.

TABLE II

Sheath Yarns Related to Suture Denier

| Overall Suture Denier | Suture Size | Number of Sheath Yarns (Broad Range) | Number of Sheath Yarns (Preferred Range) |
|---|---|---|---|
| 25 to about 80 | 7/0,8/0 | 3–12 | 3–8 |
| greater than about 80 to about 150 | 6/0 | 3–12 | 3–8 |
| greater than about 150 to about 300 | 5/0 | 4–16 | 6–14 |
| greater than about 300 to about 600 | 4/0 | 4–16 | 6–14 |
| greater than about 600 to about 950 | 3/0 | 4–16 | 6–14 |
| greater than about 950 to about 1500 | 2/0 | 6–24 | 12–20 |
| greater than about 1500 to about 2300 | 0 | 6–24 | 12–20 |
| greater than about 2300 to about 4300 | 1,2 | 6–24 | 12–20 |

It is generally preferred that they be air entangled so as to minimize snagging during braid construction. Alternatively, the sheath yarns can be provided with a twist in lieu of being air entangled.

(4) Individual Filament Denier

The individual filaments comprising each sheath yarn can vary in size from about 0.2 to about 6.0 denier, preferably from about 0.8 to about 3.0 denier and more preferably from about 1.0 to about 1.8 denier. The number of such filaments present in a particular sheath yarn will depend on the overall denier of the suture as well as the number of sheath yarns utilized in the construction of the suture. Table III sets forth some typical numbers of filaments per sheath yarn for both the broad and preferred ranges of filament denier:

TABLE III

Number of Filaments per Sheath Yarn

| approximate minimum | approximate maximum | Filament Denier |
|---|---|---|
| 45 | 450 | 0.2 |
| 15 | 150 | 0.5 |
| 5 | 50 | 1.5 |
| 3 | 40 | 1.8 |
| 1 | 15 | 6.0 |

(5) Core (optional)

For all but the lowest range of overall denier, the braided suture herein can optionally be constructed around a filamentous core which itself can be braided or which can be provided in some other configuration such as a twist, ply, cable, etc. The filament(s) comprising the core need not be as fine as those comprising the sheath yarns. It is particularly advantageous for sutures of heavier denier to possess a core.

Table IV below provides some typical core deniers for sutures of various deniers.

TABLE IV

Core Denier Related to Suture Denier

| Overall Suture Denier | Suture Size | Denier of Optional Core (Broad Range) | Denier of Optional Core (Preferred Range) |
|---|---|---|---|
| from about 25 to about 80 | 8/0,7/0 | none | none |
| greater than about 80 to about 150 | 6/0 | 0–80 | none |

TABLE IV-continued

Core Denier Related to Suture Denier

| Overall Suture Denier | Suture Size | Denier of Optional Core (Broad Range) | Denier of Optional Core (Preferred Range) |
|---|---|---|---|
| greater than about 150 to about 300 | 5/0 | 0–100 | none |
| greater than about 300 to about 600 | 4/0 | 0–125 | none |
| greater than about 600 to about 950 | 3/0 | 0–300 | 30–90 |
| greater than about 950 to about 1500 | 2/0 | 0–700 | 150–250 |
| greater than about 1500 to about 2300 | 0 | 0–1200 | 200–300 |
| greater than about 2300 to about 4300 | 1,2 | 0–2400 | 250–650 |

A suture 101 may be attached to a surgical needle 100 as shown in FIG. 2 by methods well known in the art. Wounds may be sutured by passing the needled suture through tissue to create wound closure. The needle preferably is then removed from the suture and the suture tied.

It is further contemplated that one or more clinically useful substances can be incorporated into compositions containing, or used in conjunction with the copolymers described herein. Examples of such clinically useful substances include, for example, those which accelerate or beneficially modify the healing process when applied to a surgical repair site. So, for example, the suture can carry a therapeutic agent which will be deposited at the repair site. The therapeutic agent can be chosen for its antimicrobial properties, capability for promoting repair or reconstruction and/or new tissue growth. Antimicrobial agents such as broad spectrum antibiotic (gentamycin sulfate, erythromycin or derivatized glycopeptides) which are slowly released into the tissue can be applied in this manner to aid in combating clinical and sub-clinical infections in a tissue repair site. To promote repair and/or tissue growth, one or several growth promoting factors can be introduced into the sutures, e.g., fibroblast growth factor, bone growth factor, epidermal growth factor, platelet derived growth factor, macrophage derived growth factor, alveolar derived growth factor, monocyte derived growth factor, magainin, and so forth. Some therapeutic indications are: glycerol with tissue or kidney plasminogen activator to cause thrombosis, superoxide dimutase to scavenge tissue damaging free radicals, tumor necrosis factor for cancer therapy or colony stimulating factor and interferon, interleukin-2 or other lymphokine to enhance the immune system.

It may be desirable to dye the sutures made in order to increase visibility of the suture in the surgical field. Dyes known to be suitable for incorporation in sutures can be used. Such dyes include but are not limited to carbon black, bone black, D&C Green No. 6, and D&C Violet No. 2 as described in the handbook of U.S. Colorants for Food, Drugs and Cosmetics by Daniel M. Marrion (1979). Preferably, the sutures are dyed by adding up to about a few percent and preferably about 0.2% dye, such as D&C Violet No. 2 to the resin prior to extrusion.

While specific physical characteristics will depend on the braid structure, filament denier and process parameters, sutures made from the copolymers described herein can have the following superior characteristics for the following size suture:

| Type of Suture | Size of Suture | Initial USP Modified Knot Strength (kg) | USP Modified Knot Strength After 3 Weeks Implantation In Vivo (kg) |
|---|---|---|---|
| Presently Described Copolymers | 5/0 | >1.2 | >0.5 |
| VICRYL | 5/0 | 0.93 | 0.30 |
| DEXON II | 5/0 | 1.02 | 0.23 |
| Presently Described Copolymers | 2/0 | >4.8 | >1.9 |
| VICRYL | 2/0 | 3.73 | 1.66 |
| DEXON II | 2/0 | 4.34 | 0.66 |
| Presently Described Copolymers | 1 | >8.1 | >3.0 |
| VICRYL | 1 | 6.60 | 1.99 |
| DEXON II | 1 | 7.28 | 1.25 |

In order that those skilled in the art may be better able to practice the compositions and methods described herein, the following example is given as an illustration of the preparation of block copolymers as well as of the preparation and superior characteristics of sutures made from the copolymers. It should be noted that the invention is not limited to the specific details embodied in the examples and further that all ratios or parts recited are by weight, unless otherwise indicated.

EXAMPLE

Lactide (7,000 grams) and glycolide (7,000 grams) were added to a reactor along with 3.8 grams of stannous octoate and 28.3 grams of dodecanol. The mixture was dried for about six hours with agitation under flow of nitrogen. The reactor temperature was then set at 170° C., and polymerization conducted with stirring under a nitrogen atmosphere for about 5 hours. The glycolide/lactide random copolymer was then sampled.

Glycolide (3000 grams) was added to the reactor and the setting for the temperature of the reactor was then increased to 220° C. When the temperature of the reactor reached about 200° C., 33,000 additional grams of dry glycolide were added with continued stirring. The polymerization was continued for about 166 minutes after the above addition of the 33,000 grams of glycolide. The copolymer was then extruded, pelletized and heated under vacuum to remove residual water, residual solvent and/or unreacted monomer. The resulting block copolymer contained about 90 mole percent glycolide and about 10 mole percent lactide.

Yarn containing 23 filaments having a denier in the range 34.9 to 38.6 were produced by spinning the copolymer. The filaments were dyed with about 0.2% D&C Violet No. 2. The spinning conditions employed to produce such filaments were as follows:

TABLE V

CONDITIONS OF MANUFACTURING
MULTIFILAMENT SUTURES FROM THE
BLOCK COPOLYMERS OF EXAMPLE

Extrusion Conditions

| | |
|---|---|
| pump, rpm | 36.76 |
| barrel temp., ° C., zone A | 227 |
| barrel temp., ° C., zone B | 227 |

TABLE V-continued

CONDITIONS OF MANUFACTURING
MULTIFILAMENT SUTURES FROM THE
BLOCK COPOLYMERS OF EXAMPLE

| | |
|---|---|
| barrel temp., ° C., zone C | 227 |
| mixer clamp temp., ° C. | 227 |
| pump temp., ° C. | 215 |
| block temp., ° C. | 223 |
| spinneret temp., ° C. | 223 |
| collar temp., ° C. | 265 |
| spinneret melt temp., ° C. | 229 |
| barrel pressure, psi | 930 |
| pump pressure, psi | 750 |
| spinneret pressure, psi | 1550 |
| pump size, cc per revolution | .16 |
| lube pump, rpm | 4.1 |
| Drawing (Orienti:ng) Operation Example | |
| godet 1 temp., ° C. | 70 |
| first godet, mpm | 195 |
| second godet, mpm | 1120 |
| Godet 2 temp., ° C. | 90 |
| third godet, mpm | 1100 |
| draw ratio | 5.64 |
| Post Treatment/Annealing Operation Example | |
| oven temp., ° C. | 120 |
| time (hrs.) | 18 (plus about 8 hr. heating and cooling ramps) |

Eight yarns each made from 23 filaments were braided to produce a size 5/0 multifilament suture. The braid was washed in pyrogen-free water, stretched about 4% with heating at about 135° C. and then heated under vacuum with a flow of nitrogen to remove any volatile residual monomers or contaminants. The braid was then washed again with water and with a solvent to remove any excess dye or contaminants. A coating solution of equal parts calcium stearoyl lactylate and 10/90 glycolide-caprolactone was applied to the braid to provide a coating level of about 3.5% based on the weight of the braid.

The size 5/0 suture of this Example and commercially available VICRYL sutures were tested to determine strength retention in vivo. The test was conducted as follows: each type of size 5/0 suture was knotted and implanted into female Sprague-Dawley rats. Modified U.S.P. knots were tied using sterile technique. Suture loops were formed around glass mandrels (diameter=7 mm) and secured with a surgeon's knot tied square (2=1). The ears on the knot were cut to be 25 mm long. The loop was removed from the mandrel and placed in an appropriately labeled sterile Petri dish until implantation.

Rats were euthanized at weekly intervals, the suture samples harvested and their residual strength determined. Suture strength at the various analysis intervals was compared to the initial strength of the knots prior to implantation. The results of the in vivo strength retention tests are summarized in TABLE VI.

TABLE VI

Mean Knot Strength (kg), Modified U.S.P. Knot

| | Week 1 | Week 2 | Week 3 | Week 4 | Week 5 | Week 6 |
|---|---|---|---|---|---|---|
| Example | 1.02 | 0.85 | 0.58 | 0.30 | 0.05 | 0.0 |
| VICRYL | 0.80 | 0.57 | 0.30 | 0.06 | 0.0 | 0.0 |

The size 5/0 sutures were also tested for in vivo mass loss. The details of the test procedure were as follows: each type of size 5/0 suture was implanted into female Sprague-Dawley rats through their abdominal muscles (3 loops on each side of the midline). Rats were euthanized and samples harvested at each of 8, 10, 12 and 15 weeks. All samples were fixed in formalin and the volume of suture remaining in tissue was determined. A calibrated ocular micrometer was used to measure suture diameter. An estimate of percent of suture absorbed was made by visual light-microscopic comparison of filaments remaining after one week (taken to represent starting suture size) with filaments remaining at various test intervals.

The results of the in vivo mass loss are provided in Table VII. For comparison, in vivo mass loss data for commercially available size 5/0 VICRYL sutures are also provided.

TABLE VII

Percent of Suture Absorbed Over Time

| | Week 8 | Week 10 | Week 12 | Week 15 |
|---|---|---|---|---|
| Ex. | 25 | 81 | 95 | 99 |
| Vicryl | 96 | 97 | 97 | 98 |

As the foregoing data show, the 5/0 sutures made from the copolymer of the Example exhibited increased tensile strength retention, yet exhibited no substantial decrease in the rate of mass loss compared to the presently available VICRYL sutures.

Modifications and variations of the compositions and processes disclosed herein are possible in light of the above teachings. It is therefore to be understood that changes may be made in particular embodiments described which are within the full intended scope of the invention as defined by the claims.

What is claimed is:

1. A suture comprising a sterile fiber made from a block copolymer having a first block having:
   a) a first block containing from about 40 to about 65 mole percent of repeating units derived from glycolide randomly combined with from about 60 to 35 mole percent of repeating units derived from lactide; and
   b) a second block containing of repeating units derived from glycolide and repeating units derived from lactide, the second block containing a higher proportion of repeating units derived from glycolide than the first block,
   the units derived from glycolide constituting from about 75 to about 95 mole percent of the entire block copolymer.

2. A suture as in claim 1 wherein the first block of the copolymer contains from about 40 to about 45 mole percent lactic acid ester linkages.

3. A suture as in claim 1 wherein the first block of the copolymer constitutes from about 10 to about 60 percent by weight of the entire copolymer.

4. A suture as in claim 1 wherein the block copolymer is a triblock copolymer.

5. A suture according to claim 1, wherein the suture comprises a size 1 suture having an initial U.S.P. modified knot strength greater than about 8.1 kg.

6. A suture according to claim 1, wherein the suture comprises a size 2/0 suture having an initial U.S.P. modified knot strength greater than about 4.8 kg.

7. A suture according to claim 1, wherein the suture comprises a size 5/0 suture having an initial U.S.P. modified knot strength greater than about 1.2 kg.

8. A suture according to claim 1, wherein the suture comprises a size 1 suture having a U.S.P. modified knot strength after three weeks of implantation in vivo of greater than about 3.0 kg.

9. A suture according to claim 1 further comprising a size 2/0 suture having a U.S.P. modified knot strength after three weeks of implantation in vivo greater than about 1.9 kg.

10. A suture according to claim 1, wherein the suture comprises a size 5/0 suture having a U.S.P. modified knot strength after three weeks of implantation in vivo greater than about 0.5 kg.

* * * * *